US010448817B2

(12) United States Patent
Gingras (10) Patent No.: US 10,448,817 B2
(45) Date of Patent: Oct. 22, 2019

(54) ENDOSCOPIC DEVICE INCORPORATING DIODE LASER FOR PDD, PDT, AND AF APPLICATIONS

(71) Applicant: KARL STORZ ENDOVISION, INC., Charlton, MA (US)

(72) Inventor: Joseph R. Gingras, Union, CT (US)

(73) Assignee: Karl Storz Endovision, Inc., Charlton, MA (US)

( * ) Notice: Subject to any disclaimer, the term of this patent is extended or adjusted under 35 U.S.C. 154(b) by 990 days.

(21) Appl. No.: 13/916,237

(22) Filed: Jun. 12, 2013

(65) Prior Publication Data

US 2013/0331647 A1 Dec. 12, 2013

Related U.S. Application Data

(60) Provisional application No. 61/658,618, filed on Jun. 12, 2012.

(51) Int. Cl.
| | |
|---|---|
| *A61B 1/06* | (2006.01) |
| *A61B 1/00* | (2006.01) |
| *A61B 1/04* | (2006.01) |
| *A61B 1/07* | (2006.01) |
| *A61N 5/06* | (2006.01) |
| *G02B 23/24* | (2006.01) |

(52) U.S. Cl.
CPC ........ *A61B 1/0684* (2013.01); *A61B 1/00108* (2013.01); *A61B 1/043* (2013.01); *A61B 1/0638* (2013.01); *A61B 1/0669* (2013.01); *A61B 1/07* (2013.01); *A61N 5/0601* (2013.01); *A61N 5/062* (2013.01); *G02B 23/2469* (2013.01); *A61N 2005/0651* (2013.01); *A61N 2005/0654* (2013.01)

(58) Field of Classification Search
CPC ............... A61N 5/0601; A61B 1/0684; A61B 1/00108; A61B 1/043; A61B 1/0638
USPC .................. 600/130, 131, 160, 178
See application file for complete search history.

(56) References Cited

U.S. PATENT DOCUMENTS 4,791,480 A * 12/1988 Muranaka ............... A61B 1/042
348/230.1
4,938,205 A * 7/1990 Nudelman ........... A61B 1/0008
257/E31.115

(Continued)

FOREIGN PATENT DOCUMENTS

| EP | 2561798 A1 | 2/2013 |
|---|---|---|
| WO | 9605693 A1 | 2/1996 |

OTHER PUBLICATIONS

European Search Report Application No. EP 13 17 1609 Completed: Oct. 9, 2013; dated Oct. 18, 2013 7 pages.

(Continued)

*Primary Examiner* — Timothy J Neal
*Assistant Examiner* — Jae Woo
(74) *Attorney, Agent, or Firm* — Whitmyer IP Group LLC (57) ABSTRACT

Endoscopic device incorporating diode lasers for use in PDD, PDT and AF applications. Devices according to the invention do not require an external light source, bulb lamp, or light delivery cables. Multiple laser diodes and multiple wavelengths can be employed in continuous or pulsed applications for simultaneous multi-mode diagnostic readout or simultaneous diagnostic readout and treatment.

30 Claims, 4 Drawing Sheets

(56) References Cited

U.S. PATENT DOCUMENTS

| | | | | |
|---|---|---|---|---|
| 4,953,539 | A | * | 9/1990 | Nakamura .......... A61B 1/00177 348/E5.029 |
| 4,974,076 | A | * | 11/1990 | Nakamura .............. A61B 1/05 348/71 |
| 5,278,642 | A | * | 1/1994 | Danna ............... A61B 1/00096 348/269 |
| 5,468,238 | A | | 11/1995 | Mersch |
| 5,713,364 | A | * | 2/1998 | DeBaryshe ........ A61B 1/00059 250/461.2 |
| 6,061,591 | A | * | 5/2000 | Freitag ................ A61B 5/0071 600/476 |
| 6,364,829 | B1 | * | 4/2002 | Fulghum ........... A61B 1/00009 600/160 |
| 6,482,150 | B2 | * | 11/2002 | Utsui ...................... A61B 1/05 600/178 |
| 6,640,131 | B1 | | 10/2003 | Irion et al. |
| 6,692,431 | B2 | | 2/2004 | Kazakevich |
| 6,730,019 | B2 | * | 5/2004 | Irion ....................... A61B 1/07 362/555 |
| 7,179,222 | B2 | * | 2/2007 | Imaizumi .......... A61B 1/00009 600/109 |
| 7,351,242 | B1 | | 4/2008 | Neuberger et al. |
| 8,280,496 | B2 | * | 10/2012 | Robertson .......... A61B 1/00009 600/342 |
| 8,337,400 | B2 | * | 12/2012 | Mizuyoshi .......... A61B 1/0638 600/178 |
| 8,556,806 | B2 | * | 10/2013 | Farr ..................... A61B 1/0607 600/109 |
| 9,072,454 | B2 | | 7/2015 | Irion et al. |
| 2004/0148141 | A1 | * | 7/2004 | Tsujita ............... A61B 1/00009 702/190 |
| 2004/0225222 | A1 | * | 11/2004 | Zeng .................... A61B 1/043 600/476 |
| 2005/0215911 | A1 | * | 9/2005 | Alfano .................. A61B 1/041 600/476 |
| 2006/0171693 | A1 | | 8/2006 | Todd et al. |
| 2008/0114419 | A1 | | 5/2008 | Crowley |
| 2008/0300457 | A1 | * | 12/2008 | Hosaka .............. A61B 1/00096 600/110 |
| 2009/0012358 | A1 | * | 1/2009 | Ichihashi .......... A61B 1/00105 600/110 |
| 2009/0146077 | A1 | * | 6/2009 | Moy .................... A61B 1/0638 250/458.1 |
| 2010/0198009 | A1 | * | 8/2010 | Farr ................... A61B 1/00103 600/109 |
| 2011/0018988 | A1 | * | 1/2011 | Kazakevich ....... A61B 1/00016 348/68 |
| 2011/0118547 | A1 | | 5/2011 | Erikawa |
| 2011/0235324 | A1 | | 9/2011 | Irion et al. |
| 2011/0245603 | A1 | | 10/2011 | Brannon |
| 2012/0165627 | A1 | * | 6/2012 | Yamamoto ............. A61B 1/043 600/317 |

OTHER PUBLICATIONS

European Office Action Application No. 13171609.4 dated Feb. 3, 2016 4 Pages.
Decision to Refuse European Patent Application Application No. 13171609.4 Completed Date: Nov. 23, 2017 24 Pages.
Summons to Attend Oral Proceedings Application No. 13171609.4 Completed Date: Jan. 20, 2017 5 Pages.
Summons to Attend Oral Proceedings Application No. 13171609.4 Completed Date: Mar. 15, 2017 5 Pages.

* cited by examiner

ENDOSCOPIC DEVICE INCORPORATING DIODE LASER FOR PDD, PDT, AND AF APPLICATIONS

FIELD OF THE INVENTION

The invention relates to devices for photodynamic diagnosis or treatment generally, and specifically to systems and devices incorporating diode lasers for use in PDD, PDT and AF applications.

BACKGROUND OF THE INVENTION

Auto-fluorescence (AF) is the natural emission of light by biological structures such as mitochondria and lysozomes when they have absorbed light. In some medical applications, AF can be used to illuminate structures of interest, or as a diagnostic indicator. For example, cellular AF can be used as an indicator of cytotoxicity.

Photodynamic Diagnosis (PDD) is another medical application of fluorescence. In PDD, malignant tissue can be differentiated from benign tissue by administering a suitable fluorescence marker. Typically the marker is selected such that it is preferentially absorbed by tumors. Under appropriate diagnostic lighting, the marker can be made to fluoresce, helping to define the borders of the tumor for identification and diagnosis or for removal by a surgeon, for example. In some applications, diagnostic light of varying wavelengths can be used to differentiate tissue without administering a drug.

Photodynamic Therapy (PDT) is conducted similarly to PDD, except that the drug which is administered and preferentially absorbed by malignant tissue is used in subsequent destruction of that tissue. Typically, PDT applications involve the use of a photosensitizer, a light source, and tissue oxygen. The wavelength of the light source is tuned to excite the photosensitizer in order to produce reactive oxygen species. The combination of these elements leads to the destruction of any tissues which have selectively taken up the photosensitizer and are locally exposed to light from the light source.

Prior art systems for these applications are known. One example is the Karl Storz D-Light C PDD System. This system incorporates an endoscope, such as a cystoscope used in bladder and urethra examinations. Diagnostic light is supplied to the endoscope from a separate and remote external light source using a light guide, which may be a quartz light guide or a fluid light cable, for instance. The closed end of the light cable is inserted into a socket on the light source. The open end of the light cable is connected to a light post that is a part of the endoscope.

As is typical for known systems, the light source incorporates a lamp to generate the diagnostic light. In this case, a 300 W Cermax® Lamp is used. The light source is sizeable, measuring 300 mm×164 mm×320 mm, and weighting approximately 11 kg. The lamp is a xenon arc lamp generating incoherent light, which must be replaced after an operating time of 400 hours. The light source is typically housed in a tower, which is a rack mounting system.

Another known system is disclosed in U.S. Pat. No. 6,640,131 to Irion et al., assigned to Karl Storz GmbH & Co., the content of which is incorporated herein in its entirety.

Such discrete component systems are complicated, delicate, cumbersome, and require frequent maintenance of the light source.

Other known approaches to PDT, PDD or AF endoscopy have incorporated light emitting diodes. However, these applications have used diodes at the distal end of the endoscope. Furthermore, these systems have supported limited additional functionality.

U.S. Pat. No. 7,351,242 to Neuberger et al. discloses an endoscope for PDT having low wattage diodes at the distal end. However, Neuberger et al. does not teach the use of a diode laser incorporated into the proximal end for PDT/PDD applications, does not teach synchronous video and diode pulsing for simultaneous readout of multiple diagnostic modes or treatment, and teaches away from the use of a non-distally located light source.

U.S. Pat. No. 5,468,238 to Mersch discloses an endoscope having a diode laser at the distal end for cutting or coagulating tissue. However, Mersch does not teach the use of a diode laser incorporated into the proximal end for PDT/PDD applications, does not teach synchronous video and diode pulsing for simultaneous readout of multiple diagnostic modes or treatment, and teaches away from the use of a non-distally located light source.

US Patent Publication No. 2008/0114419 to Crowley discloses a miniature light device at the distal end of an interventional device, including distally located laser diodes used for PDT. However, Crowley does not teach the use of a diode laser incorporated into the proximal end for PDT/PDD applications, does not teach synchronous video and diode pulsing for simultaneous readout of multiple diagnostic modes or treatment, and teaches away from the use of a non-distally located light source.

Other known approaches to endoscopic illumination have incorporated light emitting diodes at the proximal end of the endoscope. However, these applications have not been designed for use in PDT, PDD or AF applications, and systems have supported limited additional functionality.

U.S. Pat. No. 6,730,019 to Irion, assigned to Karl Storz GmbH & Co., discloses an endoscope for multi-color illumination having multiple light emitting diodes at the proximal end, emitting visible light of different colors which is additively mixed to provide faithful full color imaging. The diodes are used for color modulation. However, Irion does not teach the use of non-visible wavelength diodes, PDT applications, or synchronous video and diode pulsing for simultaneous readout of multiple diagnostic modes of treatment.

US Patent Publication No. 2011/0245603 to Brannon discloses a detachable external visible laser source which can be attached to the proximal end of an endoscope for use as a sighting device for aiming the endoscope. However, Brannon not teach the use of multiple different wavelength laser diodes, non-visible wavelength diodes, PDT, PDD or AF applications, video recording, or synchronous video and diode pulsing for simultaneous readout of multiple diagnostic modes or treatments.

It is therefore desired to provide a device which addresses these deficiencies.

SUMMARY OF THE INVENTION

Accordingly, it is an object of the present invention to provide a PDD, PDT, and/or AF system which improves the simplicity, ergonomics, and efficiency of the prior systems.

It is a further object of the present invention to provide a PDD, PDT, and/or AF system which replaces the light source and delivery cable with laser diodes incorporated into the endoscope.

It is a further object of the present invention to provide a PDD, PDT, and/or AF system incorporating various types of lasers.

It is a further object of the present invention to provide a PDD, PDT, and/or AF system incorporating a laser diode.

It is a further object of the present invention to provide a PDD, PDT, and/or AF system adapted for both continuous and pulsed operations.

It is a further object of the present invention to provide a PDD, PDT, and/or AF system incorporating synchronous video/diode pulsing for simultaneous readout of multiple modes.

It is a further object of the present invention to provide a PDD, PDT and/or AF system incorporating synchronous video/diode pulsing for simultaneous non-visible wavelength treatment or fluorescence diagnosis and visible wavelength diagnostic readout.

It is a further object of the present invention to provide a PDD, PDT, and/or AF system incorporating a combination of blue and white diodes in the same system.

It is a further object of the present invention to provide a PDD, PDT, and/or AF system incorporating a dual- or multiple-wavelength diode.

These and other objects of the invention are achieved by providing an endoscopy system for photodynamic applications including an endoscope having a distal end and a proximal end; a light source configured to emit light at a wavelength suitable for a photodynamic application and disposed closer to the proximal end than to the distal end; and, a light guide configured to transmit light from the light source to the distal end for illuminating tissue.

In some implementations, the light source is integral with the endoscope. Optionally, the light source may be incorporated into a unit attached to the endoscope. The light source may include a laser diode, and/or a light emitting diode.

In some implementations, the system includes focus optics disposed at the distal end. Optionally, the system includes a collimator disposed closer to the proximal end than to the distal end.

In some implementations, the system includes an imager disposed at the distal end.

In some implementations, the system includes a solid state image sensor disposed at the distal end.

In some implementations, the light source includes a dual-wavelength or multi-wavelength diode.

In some implementations, the light source includes at least two diodes or at least two p-n junctions. Optionally, the light source includes a first diode and a second diode; wherein the first diode is configured to emit light having a first wavelength and the second diode is configured to emit light having a second wavelength different from the first wavelength.

Optionally, the light source is configured to emit light having both predominantly blue and predominantly white wavelengths. Optionally, the light source is configured to emit both visible and non-visible wavelengths. Optionally, the light source includes a plurality of diodes, each configured to emit light having a different predominant wavelength. Optionally, the light source is configured to emit light at a wavelength suitable for diagnostic observation of tissue. Optionally the light source is configured to emit light at a wavelength suitable for Photodynamic Diagnosis. Optionally, the light source is configured to emit light at a wavelength which when absorbed by a biological structure will cause the biological structure to auto-fluoresce. Optionally, the light source is configured to emit light at a wavelength suitable for producing therapeutic effects in tissue. Optionally, the light emitting diode is configured to emit light at a wavelength suitable for Photodynamic Treatment.

In some implementations, the light source is configured to emit light at a wavelength which activates a drug. Optionally, the light source is configured to emit light at a wavelength which causes a drug illuminated by the light to produce reactive oxygen species. Optionally, the light source is configured to emit light at a wavelength which causes a drug illuminated by the light to produce free radicals. Optionally, the light source is configured to emit light at a wavelength which causes a drug illuminated by the light to produce singlet oxygen. Optionally, the light source is configured to emit light at a wavelength which causes a drug illuminated by the light to produce reactive oxygen species, wherein the drug is selected from the group consisting of hexaminolevulinate, porfimer sodium, aminolevulinic acid, methyl ester of aminolevulinic acid, Allumera™, Photofrin™, Visudyne™, Foscan™, Metvix™, Hexvix™, and Laserphyrin™, Antrin™, Photochlor™, Photosens™, Photrex™, Lumacan™, Cevira™, Visonac™, BF-200 aminolevulinic acid, Amphinex™ and azadipyrromethene.

In some implementations, the light source is configured to emit light pulses. Optionally, the light source is configured to emit light pulses which are synchronized with an imager. Optionally, the light source is configured to emit light pulses which are synchronized with image capturing by an imager. Optionally, the light source is configured to emit light pulses wherein at least one of the pulses has a wavelength that is different from at least one other of the pulses. Optionally, the light source is configured to emit light pulses wherein at least one of the pulses has a wavelength in the visible wavelength spectrum and at least one of the pulses has a wavelength that is not in the visible spectrum. Optionally, the light source is configured to emit light pulses wherein at least one of the pulses includes predominantly blue light, and wherein at least one of the pulses includes predominantly white light. Optionally, the light source is configured to emit light pulses which alternate among at least two different wavelengths. Optionally, the light source is configured to emit light pulses which alternate among diagnostic and therapeutic wavelengths.

In some implementations, the light source is configured to emit light pulses which alternate among at least two different wavelengths, and the pulses are synchronized with an imager such that a first image is produced under illumination under one of the wavelengths; and, a second image is produced under illumination under a different one of the wavelengths. Optionally, an image is not generated under pulses of light having photodynamic wavelengths.

In some implementations, the system includes an imager configured to produce a first image under illumination by light having a first wavelength and a second image under illumination by light having a second wavelength.

In some implementations, the system includes an imager configured to produce a first image under illumination by light having a first wavelength and configured not to produce an image under illumination by light having a second wavelength. Optionally, an image is only generated under pulses of light having a wavelength primarily suitable for diagnosis and not primarily suitable for therapy.

Other objects of the invention are achieved by providing an endoscopy system for photodynamic diagnosis including an endoscope having a distal end and a proximal end; a light source configured to emit light at a wavelength suitable for photodynamic diagnosis and disposed closer to the proximal end than to the distal end; and, a light guide configured to transmit light from the light source to the distal end for illuminating tissue.

In some implementations, the light source is integral with the endoscope. Optionally, the light source is incorporated into a unit attached to the endoscope. Optionally, the light source includes a laser diode or an LED.

Further objects of the invention are achieved by providing an endoscopy system for photodynamic treatment including an endoscope having a distal end and a proximal end; a light source configured to emit light at a wavelength suitable for photodynamic treatment and disposed closer to the proximal end than to the distal end; and, a light guide configured to transmit light from the light source to the distal end for illuminating tissue.

In some implementations, the light source is integral with the endoscope. Optionally, the light source is incorporated into a unit attached to the endoscope. Optionally, the light source includes a laser diode or an LED.

Other objects of the invention are achieved by providing a method for endoscopic photodynamic diagnosis including providing an endoscope having a distal end and a proximal end; a light source configured to emit light at a wavelength suitable for photodynamic diagnosis disposed closer to the proximal end than to the distal end; and, a light guide configured to transmit light from the light source to the distal end for illuminating tissue.

In some implementations the method includes applying a photodynamic diagnosis drug to a tissue; illuminating the tissue using the light source via the light guide; and, detecting an image of the illuminated tissue using an imaging device.

In some implementations, the light source is integral with the endoscope. Optionally, the light source is incorporated into a unit attached to the endoscope. Optionally, the light source includes a laser diode or an LED.

Other objects of the invention and its particular features and advantages will become more apparent from consideration of the following drawings and accompanying detailed description.

DETAILED DESCRIPTION OF THE INVENTION

Figure 1:
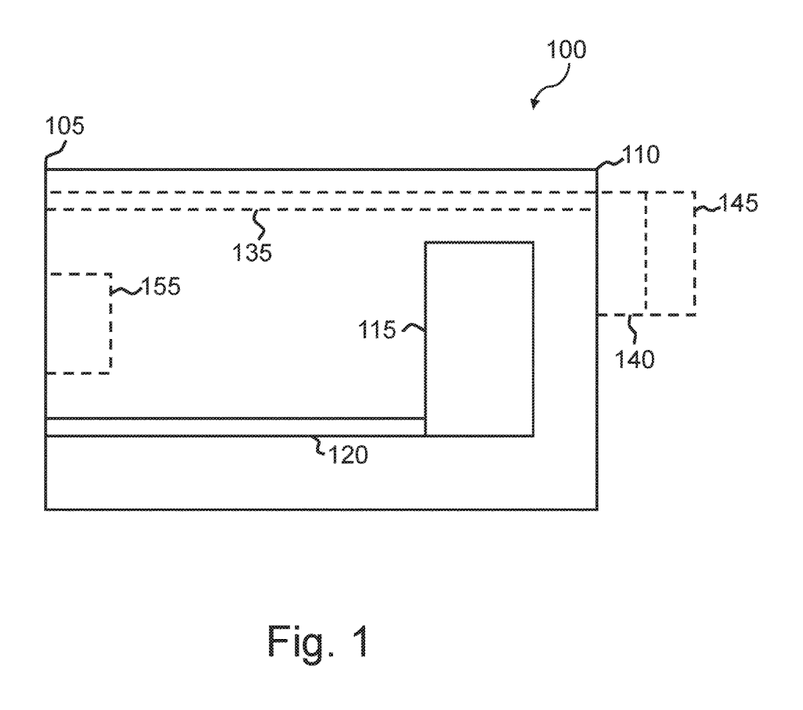
FIG. 1 is a schematic diagram of an example endoscopy system according to aspects of the invention.

FIG. 1 is a schematic diagram of an example endoscopy system having a light source according to aspects of the invention.

The system includes an endoscope 100 having a distal end 105 and a proximal end 110. A light source 115 is integral with endoscope 100. In some implementations, light source 115 is a solid state light source, such as a laser diode. Optionally, light source 115 may be detachable or replaceable. A light guide 120, which may consist of a bundle of optical fibers, for example, passes light from light source 115 to distal end 105 of endoscope 100. The light emerges from the distal end 105 and can be used to illuminate a tissue region.

Light reflected or radiating from the illuminated tissue may be detected by a camera 145 or a distal solid state imaging device 155, depending on the desired implementation.

In implementations where a camera 145 is located proximally to distal end 105, an image relaying section 135 may relay light that is reflected or radiated from observed tissues from distal end 105 to the camera 145 or solid state imaging device 155. In these implementations, image relaying section 135 may include optical fibers, rod-shaped lenses, or other suitable light communication structures.

In implementations where a solid state imaging device 155 is located at or near the distal end 105, image relaying section 135 may relay image data from solid state imaging device 155 to proximal end 110. In these implementations, image relaying section may include a wire or any other suitable medium for communication of data from solid state imaging device 155 to proximal end 110.

An image of the tissue region may optionally be viewed with the eye through an ocular 140. Camera 145 may receive the image via ocular 140, however, camera 145 may also be configured to receive the image without the use of an ocular.

Camera 145 or solid state imaging device 155 may communicate the image to a recording device, monitor, and/or analysis system (not shown).

Endoscope 100 may be of any type or configuration, including flexible/video endoscopes and rigid endoscopes. Example endoscope configurations are discussed herein with respect to FIGS. 2 and 3, although other applications of the present invention will be evident to those having skill in the art.

Light guide 120 may include any suitable structure for communicating light from proximal end 110 to distal end 105, such as optical fibers, rod lenses, or the like.

Optional ocular 140 may include an objective lens for viewing an image produced by endoscope 100, and may be configured to attach optional camera 145 to endoscope 100. In some implementations where light source 115 is integral with camera 145, ocular 140 may include structures (not shown) for communicating light from light source 115 to light guide 120. In some configurations, optional camera 145 may be attached to endoscope 100 without the use of ocular 140.

Optional camera 145 may be any suitable image sensing or recording device, and is typically a digital type camera configured to be attached to an endoscope by attachment to an ocular. It will be clear however to those having skill in the art that other types of cameras may be used with endoscope 100, with or without ocular 140. For example, in applications involving flexible video endoscopes, camera 145 may be integral with endoscope 100.

Optional solid state imaging device 155 may be any suitable solid state imaging sensor known in the art. For example, solid state imaging device 155 may include a charge coupled device (CCD) or CMOS active pixel sensor. Solid state imaging device 155 may be integral with endoscope 100, and may be disposed at or toward distal end 105. Optionally, imaging device 155 may be disposed at or toward the proximal end. An image and/or image data may be communicated from the distal end 105 to the proximal end 110 via a suitable communications medium. For example, in implementations where imaging device 155 is distally disposed, image data from the imaging device may be communicated to the proximal end 110 via a wire (not shown). In implementations where imaging device 155 is proximally disposed, light emitted or reflected by the illuminated tissue region may be communicated to imaging device 155 from the distal end using a light guide or rod lens array, for example (not shown). Various implementations may also incorporate focus optics or other optical components, for example.

Light source 115 may be powered internally or externally and may have at least one solid state light emitting device, such as a laser diode. Light source 115 may operate on a wavelength that is useful for PPD and/or PDT applications, depending upon the desired application. Such wavelengths may be selected based on their resonance with or activation of various substances, for example, tissues, drugs, or other molecules. Examples of drugs used in PDD and PDT applications include Hexaminolevulinate (Cysview®), Porfimer sodium (Photofrin®), Aminolevulinic acid (ALA or Levulan®), Methyl ester of ALA (Metvixia® cream), and other known drugs including Allumera™, Photofrin™, Visudyne™, Foscan™, Metvix™, Hexvix™, and Laserphyrin™, Antrin™, Photochlor™, Photosens™, Photrex™, Lumacan™, Cevira™, Visonac™, BF-200 ALA, Amphinex™ and Azadipyrromethenes.

The light source 115 may be capable of emitting light at multiple wavelengths. In some implementations, each wavelength may be emitted in a different mode of operation. Light source 115 may also be capable of emitting wavelengths in visible and/or non-visible spectra. Optionally, light source 115 includes multiple solid state light sources, e.g. laser diodes. Optionally, each diode can emit light at a different wavelength.

The use of solid state light emitting devices such as laser diodes can have the advantage of simplifying the system, resulting in improved ergonomics and efficiency by reducing the size and bulk over existing systems, reducing costs, simplifying cabling, enabling more efficient energy delivery, reducing fragility of the system, and addressing problems relating to short lamp life.

Optionally, light source 115 and device 100 are configured for continuous and/or pulsed operation. Optionally, light source 115, and solid state imaging device 155, camera 145, or a monitor, recording, or analysis system (not shown), can be synchronized such that images, each produced under a different wavelength, can be displayed and/or recorded by pulsing light source 115 at different wavelengths. Different wavelengths may be pulsed alternately and synchronously with video capture in order to allow simultaneous readout of multiple modes. For example, separate displays or display windows may show images under white light and blue diagnostic light, or under white light and another wavelength which causes fluorescence, for example. This can have the advantage of enabling simultaneous diagnostic observation of tissue under both non-fluorescing and fluorescing conditions, for example. This can also have the advantage of enabling diagnostic observation of tissue under visible non-fluorescing or fluorescing conditions, simultaneously with the application of non-visible wavelengths for PDT, coagulation, cautery, or cutting of tissue. This can have the further advantage of increasing the differentiability between healthy and malignant tissue by highlighting features that are optimally visible under different diagnostic wavelengths without confusion or interference caused by viewing the images additively.

Figure 2:
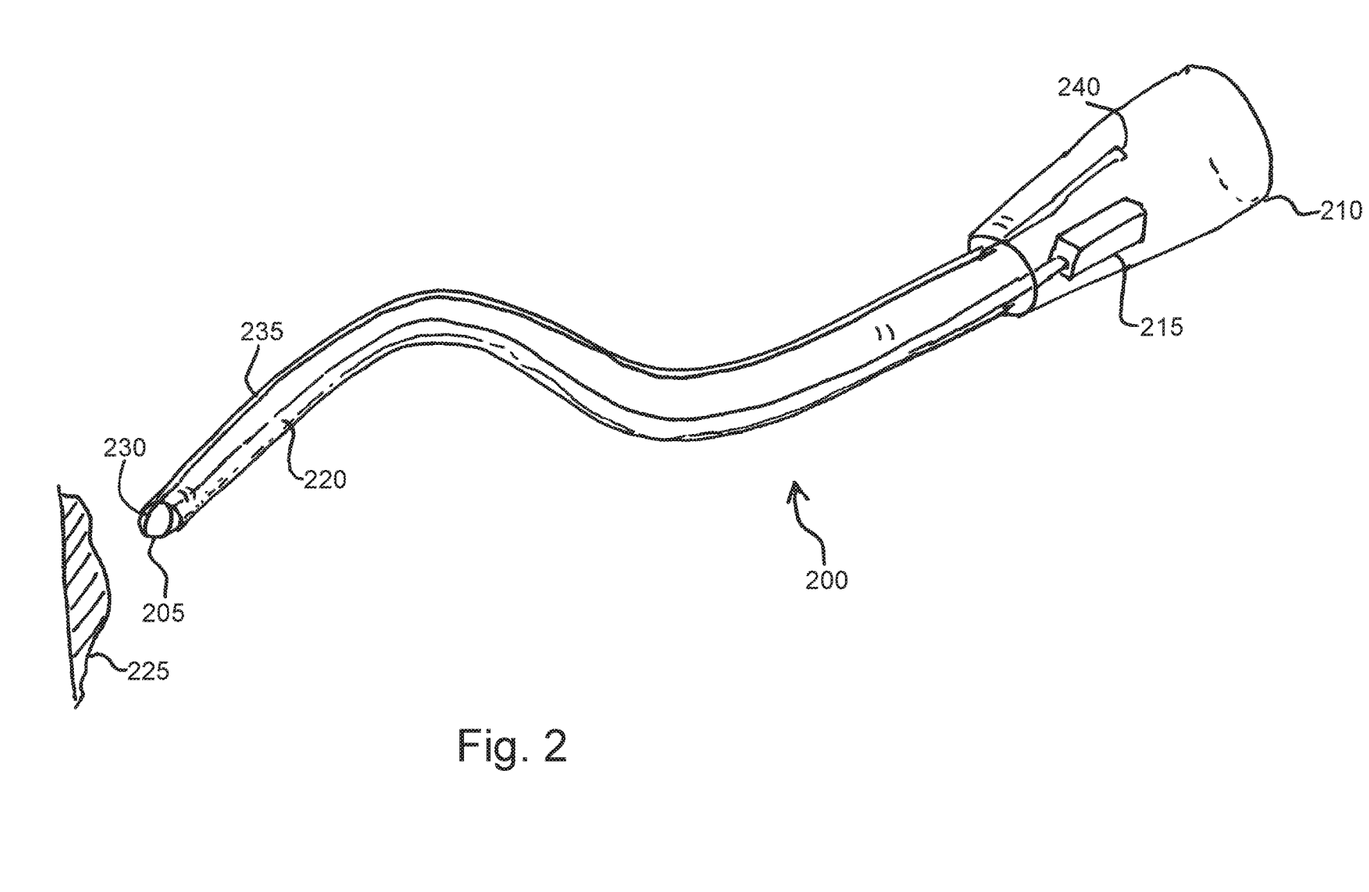
FIG. 2 is a 3D view illustrating the example endoscopy system as shown in FIG. 1, including additional features.

FIG. 2 illustrates an example endoscopy system incorporating a solid state light source according to aspects of the invention.

The system includes an endoscope 200 having a distal end 205 and a proximal end 210. Light source 215 is integral with, and incorporated into device 200. Optionally, light source 215 is detachable or replaceable. A light guide 220 in the endoscope, which may consist of a fiber bundle, for example, passes light from light source 215 to the distal end 205 of device 200. The light emerges from the distal end 205 and illuminates a tissue region 225 to be examined.

Light arriving from the illuminated tissue region 225 is received by solid state imaging device 230. A signal representing the image detected by device 230 is transmitted by an image relaying section 235 to the proximal end 210. Image relaying section 235 may be a wire or any other suitable medium for communication of data from solid state imaging device 230 to proximal end 210. Solid state imaging device 230 may include any suitable solid state image sensor, such as a charge coupled device (CCD) or CMOS active pixel sensor.

An image of tissue region 225 may be detected using solid state imaging device 230. Solid state imaging device 230 may communicate the image to a recording device, monitor, and/or analysis system via an output 240.

Light source 215 may be similar to light source 115, as described with respect to FIG. 1, and may be useable for PDD and/or PDT applications depending upon the desired implementation.

Figure 3:
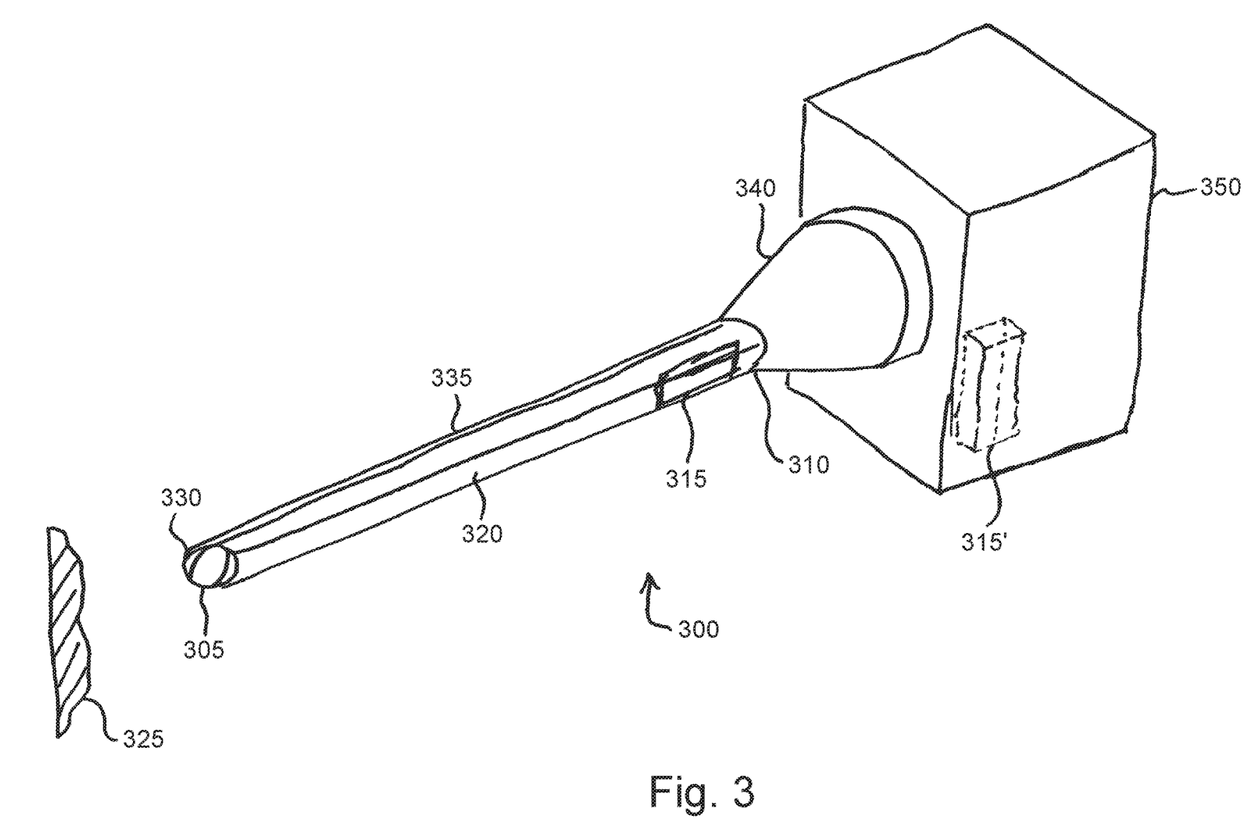
FIG. 3 is a 3D view illustrating the example endoscopy system as shown in FIG. 1, including other additional features.

FIG. 3 illustrates an example endoscopy system incorporating a solid state light source according to aspects of the invention.

The system includes an endoscope 300 having a distal end 305 and a proximal end 310. Light source 315 is integral with device 300. In other optional implementations, light source 315 may be detachable or replaceable. For example, optional light source 315' is shown incorporated into an external attached camera 350. In this example, camera 350 is attached to device 300 via an ocular 340, although those having skill in the art will understand that a camera or other imager may be used without an ocular, without departing from the invention. A light guide 320 in the endoscope, which may consist of a fiber bundle, for example, passes light from light source 315 to the distal end 305 of device 300. The light emerges from the distal end 305 and illuminates a tissue region 325.

Light emitted or reflected by the illuminated tissue region 325 enters a lens 330 of device 300. The image produced by lens 330 is guided by an image relaying section 335 to the proximal end 310. Optionally, the image may be detected by a solid state imaging sensor (not shown) proximal to, or in place of lens 330.

The image of tissue region 325 may be viewed with the eye through ocular 340, may be detected by camera 350 or a solid state imaging device (not shown), and/or may be communicated to a recording device, monitor, and/or analysis system (not shown).

Light source 315 may be similar to light source 115, as described with respect to FIG. 1, and may be useable for PDD and/or PDT applications depending upon the desired implementation.

Image relaying section 335 may include relay lenses including rod-shaped lenses or may include optical fibers. Image relaying section 335 may also incorporate various combinations of optics for collimation and focus of light.

Figure 4:
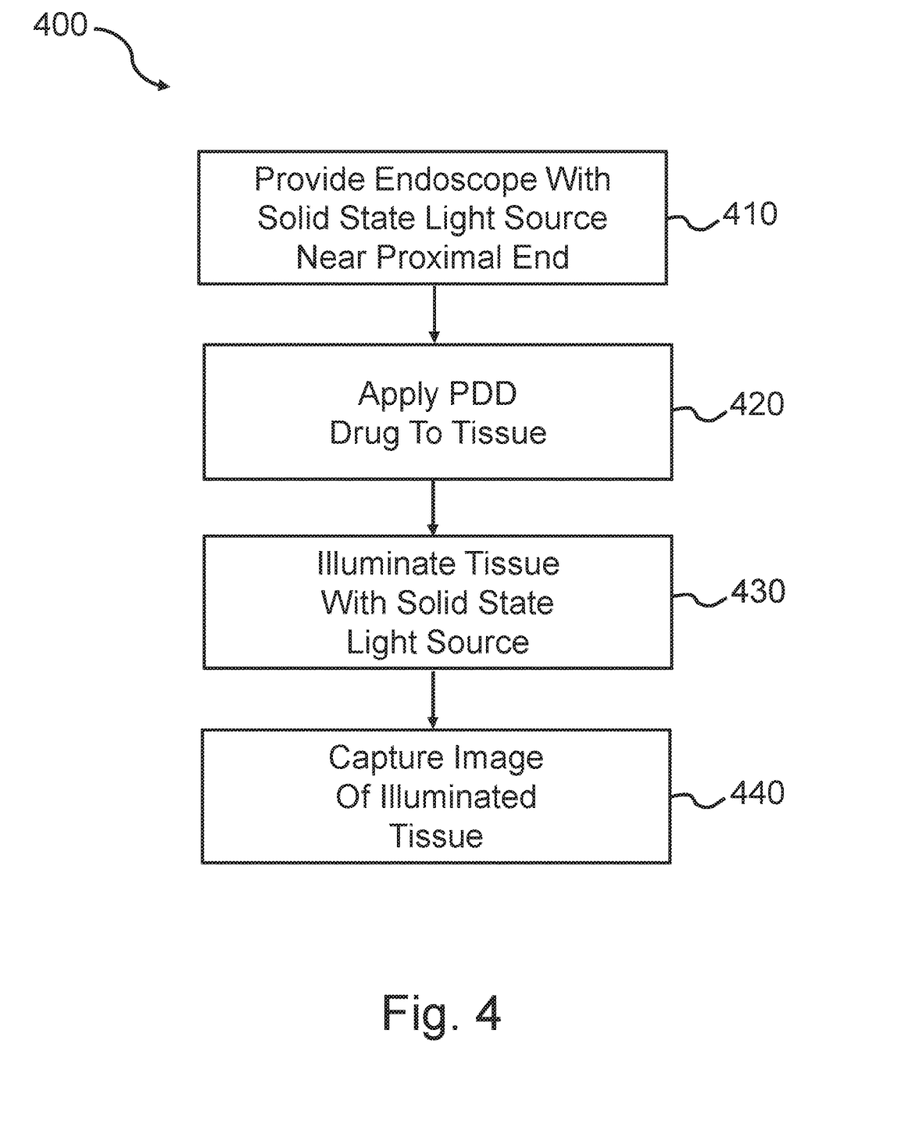
FIG. 4 is a flow chart illustrating an example photodynamic diagnosis method using the system of FIG. 1, according to aspects of the invention.

FIG. 4 is a flow chart illustrating an example photodynamic diagnosis method 400 using the system of FIG. 1, according to aspects of the invention.

In step 410, an endoscope is provided having a solid state light source that is configured to emit light at a wavelength suitable for photodynamic diagnosis, and which is disposed closer to a proximal end than to a distal end of the endoscope, and a light guide configured to transmit light from the light source to the distal end for illuminating a tissue region.

In step 420, a photo diagnosis drug is applied to a tissue region to be observed.

In step 430, the tissue region to be observed is illuminated using the solid state light source.

In step 440, an image of the illuminated tissue is detected using an imaging device such as those described with respect to other figures herein, such as a solid state imaging chip or a camera.

Although the invention has been described with reference to a particular arrangement of parts, features and the like, these are not intended to exhaust all possible arrangements or features, and indeed many modifications and variations will be ascertainable to those of skill in the art.

What is claimed is:

1. An endoscopy system, comprising:
   an endoscope having a distal end and a proximal end;
   at least one laser diode closer to the proximal end than to the distal end, the at least one laser diode configured to emit a first pulse of light at a first wavelength during a first predetermined period of time, and a second pulse of light at a second wavelength during a second predetermined period of time, wherein the first wavelength and the second wavelength are different from one another and at least one of the first wavelength and the second wavelength is suitable for a photodynamic application, and wherein the first predetermined period of time occurs before or after the second predetermined period of time;
   a light guide disposed within the endoscope, the light guide configured to transmit light from the at least one laser diode to the distal end for illuminating a tissue; and
   an imager disposed relative to the endoscope and synchronized with the at least one laser diode such that the imager is configured to (i) capture a first image of the tissue during the first predetermined period of time, and (ii) capture a second image of the tissue during the second predetermined period of time.

2. The system of claim 1, wherein the at least one laser diode is integral with the endoscope.

3. The system of claim 1, wherein the at least one laser diode is incorporated into a unit attached to the endoscope.

4. The system of claim 1, further comprising focus optics disposed at the distal end.

5. The system of claim 1, further comprising a collimator disposed closer to the proximal end than to the distal end.

6. The system of claim 1, wherein the imager is disposed at the distal end.

7. The system of claim 6, further comprising a solid state image sensor disposed at the distal end.

8. The system of claim 1, wherein the at least one laser diode comprises at least one dual-wavelength laser diode.

9. The system of claim 1, wherein the at least one laser diode comprises at least one multi-wavelength laser diode.

10. The system of claim 1, wherein the at least one laser diode comprises at least two laser diodes.

11. The system of claim 1, wherein the at least one laser diode comprises at least two p-n junctions.

12. The system of claim 1, wherein the at least one laser diode comprises a first laser diode and a second laser diode; and
   wherein the first laser diode is configured to emit the first pulse of light and the second laser diode is configured to emit the second pulse of light.

13. The system of claim 1, wherein the at least one laser diode is configured to emit light having both predominantly blue and predominantly white wavelengths.

14. The system of claim 1, wherein the at least one laser diode is configured to emit both visible and invisible wavelengths.

15. The system of claim 1, wherein the at least one laser diode comprises a plurality of laser diodes, each configured to emit light having a different predominant wavelength.

16. The system of claim 1, wherein the at least one laser diode is configured to emit at least one wavelength suitable for diagnostic observation of tissue.

17. The system of claim 1, wherein the at least one laser diode is configured to emit at least one wavelength suitable for Photodynamic Diagnosis.

18. The system of claim 1, wherein the at least one laser diode is configured to emit at least one wavelength which, when absorbed by a biological structure, will cause the biological structure to auto-fluoresce.

19. The system of claim 1, wherein the at least one laser diode is configured to emit at least one wavelength suitable for producing therapeutic effects in tissue.

20. The system of claim 1, wherein the at least one laser diode is configured to emit at least one wavelength suitable for Photodynamic Treatment.

21. The system of claim 1, wherein the at least one laser diode is configured to emit at least one wavelength which activates a drug.

22. The system of claim 1, wherein the at least one laser diode is configured to emit at least one wavelength which causes a drug illuminated by the at least one wavelength to produce reactive oxygen species.

23. The system of claim 1, wherein the at least one laser diode is configured to emit at least one wavelength which causes a drug illuminated by the at least one wavelength to produce free radicals.

24. The system of claim 1, wherein the at least one laser diode is configured to emit at least one wavelength which causes a drug illuminated by the at least one wavelength to produce singlet oxygen.

25. The system of claim 1, wherein the at least one laser diode is configured to emit at least one wavelength which causes a drug illuminated by the at least one wavelength to produce reactive oxygen species, wherein the drug is selected from the group consisting of hexaminolevulinate, porfimer sodium, aminolevulinic acid, methyl ester of aminolevulinic acid, Allumera™, Photofrin™, Visudyne™, Foscan™, Metvix™, Hexvix™, and Laserphyrin™, Antrin™, Photochlor™, Photosens™, Photrex™, Lumacan™, Cevira™, Visonac™, BF-200 aminolevulinic acid, Amphinex™ and azadipyrromethene.

26. The system of claim 1, wherein the at least one laser diode is configured such that the first wavelength is in the visible spectrum and the second wavelength is not in the visible spectrum.

27. The system of claim 1, wherein the at least one laser diode is configured such that the first pulse of light includes predominantly blue light, and the second pulse of light includes predominantly white light.

28. The system of claim 1, wherein the at least one laser diode is configured to emit light pulses which alternate among diagnostic and therapeutic wavelengths.

29. The system of claim 1, wherein the imager is changeable between a capture state, in which the imager is configured to capture the first image and the second image of the tissue, and a non-capture state, in which the imager is not configured to capture an image of the tissue.

30. The system of claim 29, wherein the imager is synchronized with the at least one laser diode such that the imager is (a) configured to be in the capture state during the first predetermined period of time and the second predetermined period of time, and (b) configured to automatically change to the non-capture state during a third predetermined period of time occurring between the first predetermined period of time and the second predetermined period of time.

* * * * *